United States Patent
Feng et al.

(10) Patent No.: US 9,695,181 B2
(45) Date of Patent: Jul. 4, 2017

(54) HYDROXIMIC ACID DERIVATIVES AND MEDICAL APPLICATIONS THEROF

(71) Applicants: Double Rider Medicine Co., LTD., Jiangxi (CN); Zixia Feng, Jiangsu (CN)

(72) Inventors: Zixia Feng, Jiangsu (CN); Zhenghong Cao, Jiangxi (CN)

(73) Assignees: Zixia Feng, Jiangsu (CN); DOUBLE RIDER MEDICINE CO., LTD., Jiangxi (CN)

( * ) Notice: Subject to any disclaimer, the term of this patent is extended or adjusted under 35 U.S.C. 154(b) by 0 days.

(21) Appl. No.: 14/909,553

(22) PCT Filed: Aug. 11, 2014

(86) PCT No.: PCT/CN2014/084068
§ 371 (c)(1),
(2) Date: Feb. 2, 2016

(87) PCT Pub. No.: WO2015/021894
PCT Pub. Date: Feb. 19, 2015

(65) Prior Publication Data
US 2016/0176879 A1    Jun. 23, 2016

(30) Foreign Application Priority Data

Aug. 14, 2013  (CN) .......................... 2013 1 0353591

(51) Int. Cl.
*C07D 487/04*    (2006.01)
(52) U.S. Cl.
CPC .................................. *C07D 487/04* (2013.01)

(58) Field of Classification Search
CPC .................................................. C07D 487/04
See application file for complete search history.

(56) References Cited

PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
HHS Public Access. "Histone Deacetylase Inhibitors in Clinical Studies as Templates for New Anticancer Agents." © Mar. 2002. Available from: <http://www.ncbi.nlm.nih.gov/pmc/articles/PMC4372801/pdf/nihms669485.pdf >.*

* cited by examiner

*Primary Examiner* — Noble Jarrell
*Assistant Examiner* — John S Kenyon
(74) *Attorney, Agent, or Firm* — Vidas, Arrett & Steinkraus, P.A.

(57) ABSTRACT

The present invention relates to a kind of new hydroximic acid derivatives, in particular, hydroximic acid derivatives of pyrazolopyrimidine and their medical applications, which have inhibition to histone deacetylase 1 and two kinds of tyrosine kinases (vascular endothelial cell growth factor receptors as well as platelet-derived growth factor receptors) simultaneously, and thus can be used for treatment of diseases related to those three kinds of enzymes. This kind of compounds both exerts a synergistic effect sufficiently to increase biological activity, and avoids problems caused by different properties and metabolisms, therefore is more practical and has good prospects.

18 Claims, No Drawings

HYDROXIMIC ACID DERIVATIVES AND MEDICAL APPLICATIONS THEROF

TECHNICAL FIELD

The present invention belongs to the bio-medicine field, in particular relates to a kind of hydroximic acid derivatives and medical applications thereof.

BACKGROUND OF INVENTION

Tyrosine kinase is a kind of proteins with tyrosine kinase activity, and can catalyze the transferring of phosphoric acid groups from ATPs to tyrosine residues of many important proteins to cause phosphorylation of these important proteins such that the downstream signal transduction pathways are activated. Protein tyrosine kinase plays a very important role in the intracellular signal transduction pathways, it regulates a series of physiological and biochemical processes such as growth, differentiation and death of cell bodies. Protein tyrosine kinase dysfunction may cause a series of diseases including tumors and eye diseases.

The occurrence, development and metastasis of many tumors as well as formation of tumor neovascularization have an extremely close relationship with abnormal expressions of tyrosine kinase. Especially, some tyrosine kinase receptors have abnormal expression in solid tumors, wherein vascular endothelial cell growth factor receptors (VEGFRs) present high expression in many tumor cells and tumor vascular endothelial cells, and platelet-derived growth factor receptors (PDGFRs) have abnormal expression in tumor stromal fibroblasts. The autocrine loop formed by ligands and receptors of tyrosine kinase directly participate in the occurrence and development of tumor cells, for example, vascular endothelial cell growth factor receptor (VEGFRs) exists in melanoma; platelet-derived growth factor receptors (PDGFRs) are present in gliomas; and stem cell growth factor receptors (KIT) resides in small cell lung cancer, and the like. Besides, similar loop also exists in meningiomas, neuroendocrine tumors, ovarian cancer, prostate cancer and pancreatic cancer. This loop has a very close relationship with the occurrence and development of tumors.

Moreover, the occurrence, development and metastasis of solid tumors depend on formation of tumor neovascularization which provides essential nutrients and oxygen for the growth of tumor. Tumor angiogenesis is an important process for invasion, migration and proliferation of tumor cells. Vascular endothelial growth factor receptor (VEGFR) family and platelet derived growth factor receptor (PDGFR) family are directly related to the occurrence and development of tumor and formation of tumor angiogenesis. Vascular endothelial growth factor (VEGF) known as the most powerful vascular penetrating agent and endothelial cell specific mitogen, plays an important role in the proliferation, migration and angiogenesis of endothelial cells. The expression level of vascular endothelial growth factor (VEGF) and the vascularization degree of tumor tissue show a significant positive correlation. VEGF mainly acts on high affinity receptors VEGFR-1 and KDR in endothelial cells which have different signal transduction pathways such that tyrosine kinase is phosphorylated to play its biological action. KDR plays a key role in growth, metastasis and angiogenesis of tumor. Platelet derived growth factor (PDGF) and its receptor (PDGFR) involves with the pathogenesis of multiple tumors and play important roles in angiogenesis. Platelet derived growth factor (PDGF) shows its cell biological effect via its receptor (PDGFR). PDGFR maintains the integrality of vascular wall and promotes the formation of tumor neovascularization by regulating the proliferation and migration of vascular wall perithelial cells and vascular smooth muscle cells. In addition, the growth of tumor is promoted by changing the microenvironment within tumor.

Due to that the abnormal expression of tyrosine kinase is very closely related to the occurrence, development and metastasis of tumor as well as formation of tumor neovascularization, drug research and development targeting tyrosine kinase has become a focus of international research of anti-tumor drugs. In particular, it is a new strategy to treat cancer that targeting neovascularization to inhibit the formation of tumor angiogenesis and block the nutrition supply and migration path of tumor to prevent the growth and metastasis of tumor. The abnormal expression of KDR or PDGFR receptors plays a key role in the formation of tumor neovascularization, and therefore KDR and PDGFR receptors have become the most ideal target for anticancer drug therapy. Moreover, two anti-tumor drugs Sorafenib and Sunitinib (SU11248) mainly inhibiting KDR and PDGFR receptor tyrosine kinases, approved by the US Food and Drug Administration (FDA), have fully demonstrated their anti-tumor therapeutic effect with high curative effect and fewer side effects in clinical practice.

Histone deacetylase (HDACs) is a kind of metalloprotease, which plays a key role in chromosome structure modification and gene expression modulation. In cancer cells, overexpression of HDACs leads to increasing of binding force between histone and DNA such that abnormally allosteric chromosome occurs. At the same time, expression of cell cycle inhibitory factor is inhibited, and stability and binding capacity with DNA of tumor suppressor gene p53 decrease, whereas expression of hypoxia inducible factor-1 (HIF-1) and vascular endothelial growth factor (VEGF) increases. In mammalian cells, the balance between acetylation and deacetylation plays a key role in gene transcription and the function of different cellular proteins. Acetylation of histone is regulated by histone acetyltransferases (HATs) and histone deacetylase (HDACs). The dynamic balance between HDACs and HATs controls the structure of chromatin and expression of genes, and the dysfunction thereof is one of the important molecular mechanisms of tumor development. HDACs belong to the super family of deacetylases, and have four types, type I, II, III and IV. At present, type I HDACs is most studied. Type I HDACs includes HDAC1, HDAC2, HDAC3 and HDAC8. HDACs play an important role in chromatin remodeling, gene repression, regulation of cell cycle and differentiation. Dysfunction of histone deacetylase in tumor cell may lead to gene transcription inhibition and inhibit expression of cancer suppressor genes. High expression of HDAC1 in tumor cells can significantly increase the proliferation ability of tumor cells, and high expression of HDAC1 can affect the extracellular matrix such that migration and invasiveness of tumor cells is enhanced significantly. It is reported that HDAC1mRNA levels and protein levels are highly expressed in gastric cancer tissues, prostate cancer tissues, colon cancer tissues and liver cancer tissues, and are correlated with TNM stage and lymph node metastasis of tumors. It is found by study that inhibiting HDACs activity can effectively inhibit cancer cell proliferation, induce cell cycle arrest and promote cell apoptosis, and therefore, HDACs becomes a new target of anticancer drug design, and developing HDAC inhibitor (HDACi) is considered as an effective strategy for cancer therapy. Micromolecule HDACi of hydroxamic acids is a kind of HDACi been paid much attention in recent years, which demonstrates a good anti-tumor activity both in vivo and in vitro. In 2006, the first hydroxy acid HDACi, SAHA (generic name: Vorinostsat; commodity names: Zolinza, 伏立诺他) approved by the United States FDA is used for treating skin T cell lymphoma. Subsequently, more and more HDACi enter into the clinical as treatment and adjuvant therapy for solid tumors such as colon cancer, lung cancer and the like, and malignancies of the blood system such as leukemia and lymphoma, etc.

It is also found in recent studies that combined utilization of targeted drugs has a better effect. Two drugs with different targets may work better in the same combined drugs.

In a study disclosed in *Cancer Research* (Qian D Z, Wang X, Kachhap S K, Kato Y, Wei Y, Zhang L, et al. The histone deacetylase inhibitor nvp-laq824 inhibits angiogenesis and has a greater antitumor effect in combination with the vascular endothelial growth factor receptor tyrosine kinase inhibitor ptk787/zk222584; *Cancer Res* 2004; 64:6626-34), such combination effect was proved in a mouse and cell lines models by researchers. These preliminary results showed very good prospects: the two different drugs target the development process of cancers in these two kinds of cells in a manner of "continuous strike".

Researcher of Johns Hopkins Kimmel Cancer Center believed that the single use of anti angiogenesis drugs in human clinical researches is difficult to achieve the desired effect on the target tumor. Previous studies have indicated that a kind of drugs that can normalize DNA winding may also affect the growth of blood vessels. Dr. Roberto Pili suggests that combination of these two kinds of drugs may have a greater impact on the development of cancers.

An anti-angiogenic drug called PTK787/ZK222584 was chosen by researchers to carry out the research, and this drug can inhibit the function of VEGF (vascular endothelial growth factor) proteins which may lead to cascade reactions of cell signal promoting angiogenesis. Such VEGF inhibitors and histone deacetylation (HDAC) inhibitors are used in combination. Cancer cells can take the acetyl groups away from histones resulting in that DNAs wrap together all the time, and therefore the activation of genes is inhibited. By utilizing histone deacetylation (HDAC) inhibitors to block the function of displacing the acetyl groups of HDACs, this error may be reversed and it is able to unfold DNAs and produce the desired gene product.

It is found in the research that the combination use of VEGF inhibitors and HDAC inhibitors NVP-LAQ824 may achieve 51% inhibition of cultured endothelial cells (that is twice of the effect when using the two drugs alone). In mouse models, this drug combination may induce 60% inhibition of new blood vessel formation, whereas the single use may induce 50% inhibition. The tumor growth inhibition ratios in the mouse suffered from a prostate cancer are 35 and 75%, respectively. This inhibition ratio is 85% when combination use. The two inhibitors respectively exhibited 54% and 60% growth inhibitions on tumors of mouse suffered from a breast cancer, whereas combination treatment showed 80% inhibition on tumor growth.

Combination medication of anti-VEFG monoclonal antibody Bevacizumab and HDAC inhibitor Valproic ACI combination has been carried out in Phase I clinical trials to provide synergistic effects and enhance drug efficacies for the treatment of intestinal cancer, gastric cancer and prostate cancer (*J Clin Oncol* 29: 2011), which showed better curative effects than single medication.

As mentioned above, the combination of drugs with different targets produces a better curative effect than single medication; however, there are still problems in hybrid applications of different drugs due to their different properties and metabolisms, thereby affecting the effects of the drugs.

SUMMARY

The present invention is intended to overcome the deficiencies of the prior art and provides a hydroxamic acid derivatives, which has three important targets in a body, exerts a synergistic effect sufficiently to increase biological activity and avoids problems caused by different properties and metabolisms.

The invention also provides the use of the new hydroxamic acid derivatives in preparation of medicines treating diseases mediated by tyrosine kinase and/or histone deacetylase.

To solve the above technical problems, the present invention employs the following technical scheme:

A compound of formula I, and a pharmaceutically acceptable salt, a hydrate, a pro-drug and a metabolite produced in any type of metabolism thereof,

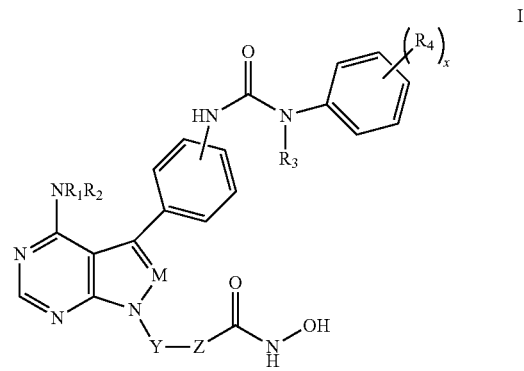

in formula I, $R_1$, $R_2$ and $R_3$ are independently selected from hydrogen, alkyl and hetero alkyl;

$R_4$ is selected from the group consisting of: halogen; hydroxyl; sulfhydryl; cyano; amino or alkyl-substituted amino; nitryl; $C_1$-$C_6$ alkyl unsubstituted or substituted by one or more of halogen, hydroxyl, sulfhydryl, cyano, amino, alkyl-substituted amino and nitryl; $C_1$-$C_6$ alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; $OCOR_9$; $NHC(=O)OCH_3$; $NHC(=O)OCH_2CH_3$;

M is N or CH;

Y is $CH_2$, $CH(CH_3)$ or $C=O$;

Z has a straight-chain structure consisting of 3-12 atoms and connecting Y and carbonyl of hydroximic acid of formula I;

x is an integer between 0 and 5;

$R_5$, $R_6$, $R_7$, $R_8$ and $R_9$ are independently selected from $C_1$-$C_6$ alkyl unsubstituted or substituted by halogen.

According to a specific aspect of the present invention: in formula I, $R_1$, $R_2$ and $R_3$ are independently selected from hydrogen or $C_1$-$C_3$ alkyl;

$R_4$ is selected from the group consisting of: fluoro, chloro, bromo, iodo, hydroxy, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, C(=O)CH₃, C(=O)CH₂CH₃, C(=O)NHCH₃, C(=O) NHCH₂CH₃, NHC(=O)OCH₃, NHC(=O)OCH₂CH₃, NHCH₃, N(CH₃)₂, and NHCH₂CH₃;

x is 0, 1, 2, 3 or 4;

M, Y and Z are defined as above.

Preferably, in formula I, x is 1 or 2.

According to a preferable aspect, the straight-chain structure consists of 3-8 carbon atoms as well as 0-4 oxygen atom(s) and/or nitrogen atom(s). Taking the activity of compounds into account, more preferably, the straight-chain structure consists of 4-7 carbon atoms as well as 0-2 oxygen atom(s) and/or nitrogen atom(s). Most preferably, the straight-chain structure consists of 5 or 6 carbon atoms as well as 0-1 oxygen atom and/or nitrogen atom. When the straight-chain structure contains nitrogen atom or oxygen atom, the activity reduces relatively, but the bio-availability may be higher.

Preferably, the straight-chain structure consists of 4-8 atoms.

According to a specific aspect of the present invention, the straight-chain structure is a saturated or unsaturated $C_3$-$C_8$ alkyl straight chain uninterrupted or interrupted by 1-2 oxygen atom(s) and/or nitrogen atom(s). Preferably, the straight-chain structure is a saturated or unsaturated $C_5$-$C_7$ alkyl straight chain uninterrupted or interrupted by 1-2 oxygen atom(s) and/or nitrogen atom(s).

Further, in formula I, Z may also include one or two branch chain(s) connecting with the central section of the straight-chain structure, the branch chain(s) being a $C_1$-$C_6$ alkyl unsubstituted or substituted by halogen. Further, the branch chain(s) is(are) methyl, ethyl or propyl.

According to a specific and preferable aspect of the present invention, in formula I, Z is (CH₂)₅, (CH₂)₆, (CH₂)₇, CH₂ CH₂TCH₂ CH₂ CH₂, CH₂ CH₂TCH₂ CH₂ or CH₂ CH₂ CH₂TCH₂ CH₂ CH₂, wherein T is O or NR₁₀, NR₁₀ is hydrogen, methyl, ethyl or propyl.

According to another preferable aspect of the present invention, the compound has a structure as shown in formula II:

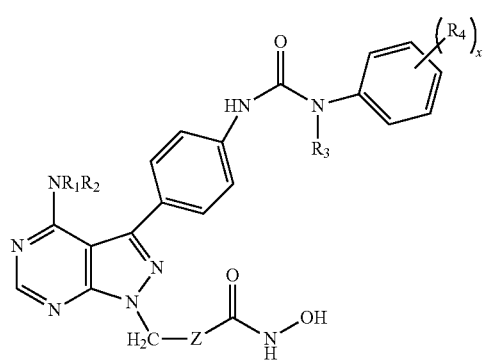

II in formula II,

R₁, R₂ and R₃ are independently selected from hydrogen or $C_1$-$C_3$ alkyl;

R₄ is selected from the group consisting of: fluoro, chloro, bromo, iodo, hydroxy, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, C(=O)CH₃, C(=O)CH₂CH₃, C(=O)NHCH₃, C(=O) NHCH₂CH₃, NHC(=O)OCH₃, NHC(=O)O CH₂CH₃, NHCH₃, N(CH₃)₂, and NH CH₂CH₃;

Z has a straight structure connecting methylene and carbonyl, the straight-chain structure being a saturated or unsaturated $C_3$-$C_8$ alkyl straight chain uninterrupted or interrupted by 1-2 oxygen atom(s) and/or nitrogen atom(s);

x is 0, 1, 2, 3 or 4.

A representative compound of the present invention is a compound as shown in formula IIa, IIb, IIc or IId.

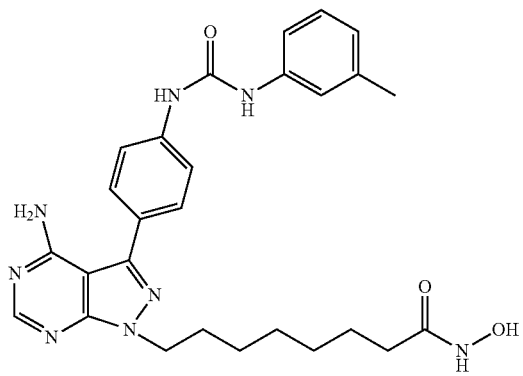

IIa

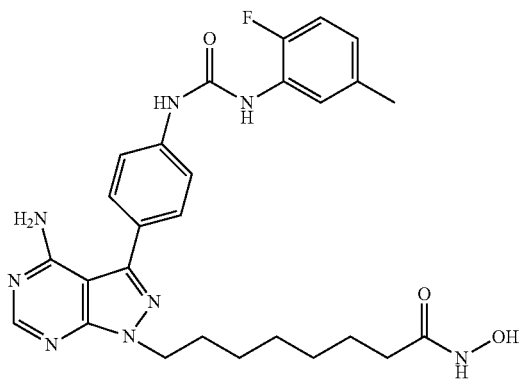

IIb

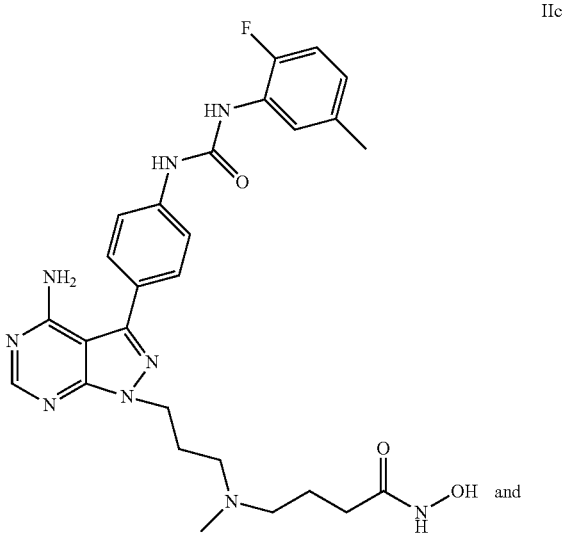

IIc and

-continued

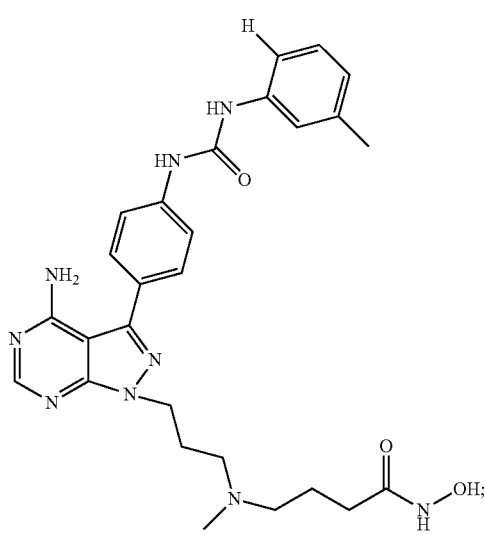
IId

According to the present invention, the compound includes not only a single compound, but also comprises various mixtures of compounds, the structure of which satisfies the requirements of formula I, as well as different isomers of the same compound such as racemates, enantiomers, diastereomers and the like. The pharmaceutically acceptable salts of compound of formula I include, but are not limited to, hydrochloride, hydrobromide, phosphate, sulfate, acetate, trifluoroacetate, maleate, methanesulfonate, benzenesulfonate, benzoate, methyl besylate, succinate, fumarate, tartrate, gallate, citrate and the like. The "pro-drug of compound of formula I" refers to a substance which can be converted into at least one compound of formula I or salts thereof by metabolic or chemical reactions in volunteers when administered by using appropriate methods.

According to the present invention, a hetero alkyl refers to alkyl substituent containing hetero atoms.

According to the present invention, in formula I, Z may include only the straight chain structure, or may also have a branch chain or a ring that connects with the straight chain structure.

The compound provided by the present invention is a new hydroximic acid derivatives, in particular, hydroximic acid derivatives of pyrazolopyrimidine, which have inhibition on a histone deacetylase 1 (HDAC1) and two kinds of tyrosine kinases, vascular endothelial cell growth factor receptor 2 (VEGFR2) as well as platelet-derived growth factor receptor-β (PDPDGFR-β) simultaneously, and thus may be used for treatment of diseases related to those three kinds of enzymes. Therefore, the present invention particularly relates to use of the compound of formula I, the pharmaceutically acceptable salt thereof, the hydrate, the pro-drug thereof and the metabolite thereof produced in any type of metabolism in preparation of medicines treating diseases mediated by tyrosine kinase and/or histone deacetylase.

Another technical scheme employed by the present invention is: a pharmaceutical composition for treating diseases mediated by tyrosine kinase and/or histone deacetylase, the effective constituents of which contains at least the compound of formula I and the pharmaceutically acceptable salt, the hydrate, the pro-drug and the metabolite produced in any type of metabolism thereof.

According to the present invention, the diseases mediated by tyrosine kinase and/or histone deacetylase comprise malignancies and eye diseases associated with pathological neovascularization. Malignancies include, but not limited to, kidney cancer, liver cancer, colon cancer, gastrointestinal stromal tumor, lung cancer, breast cancer, pancreatic cancer, neural glial tumor, lymph cancer, fibrosarcoma, ovarian cancer, leukemia and prostate cancer, etc. Eye diseases include age-related macular degeneration, diabetic retinopathy and neovascular glaucoma and the like.

The compound according to the present invention may be obtained by using conventional synthetic methods in the art of organic synthesis.

The present invention further provides an intermediate for preparing the compound of formula I having a structure as shown in formula III or IV:

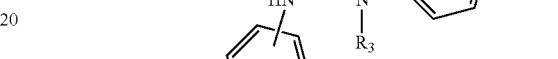

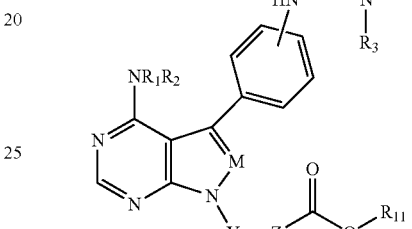

in formula III, $R_3$, $R_4$, x, M, Y and Z are defined as in formula I, $R_{11}$ is $C_1$-$C_6$ alkyl, and $R_1$ and $R_2$ are amino protection groups or defined as in formula I;

in formula IV, M, Y and Z are defined as in formula I, X is chloro, bromo or iodo, $R_{11}$ is $C_1$-$C_6$ alkyl, and $R_1$ and $R_2$ are amino protection groups or defined as in formula I;

According to a specific aspect, in formulas III and IV, $R_{11}$ is methyl or ethyl.

The present invention further provides a preparing method of the compound of formula I, which comprises a step of producing the compound of formula I by making the compound of formula III to react with hydroxylamine in a solvent, and the reaction equation is as follow:

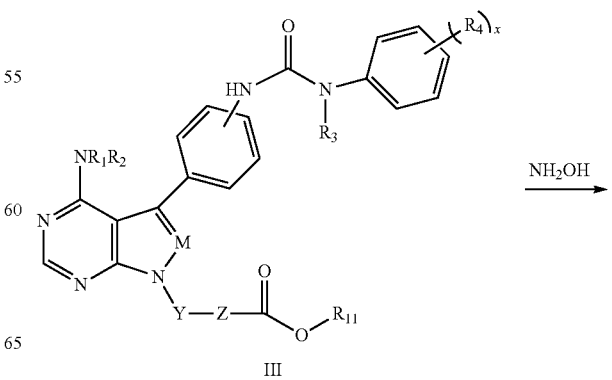

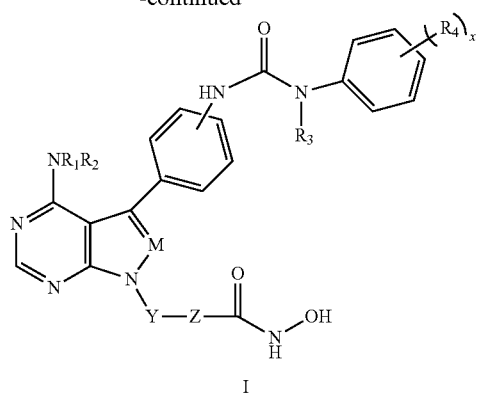

in formula III, $R_3$, $R_4$, x, M, Y and Z are defined as in formula I, $R_{11}$ is $C_1$-$C_6$ alkyl; and when neither of $R_1$ and $R_2$ is not hydrogen, $R_1$ and $R_2$ are defined as in formula I; and when at least one of $R_1$ and $R_2$ is hydrogen, $R_1$ and $R_2$ are defined as in formula I, or at least one of $R_1$ and $R_2$ is amino protection group.

Further, the preparing method comprises a step of producing the compound of formula III by making the compound of formula IV to react with a compound of formula V, and the reaction equation is as follow:

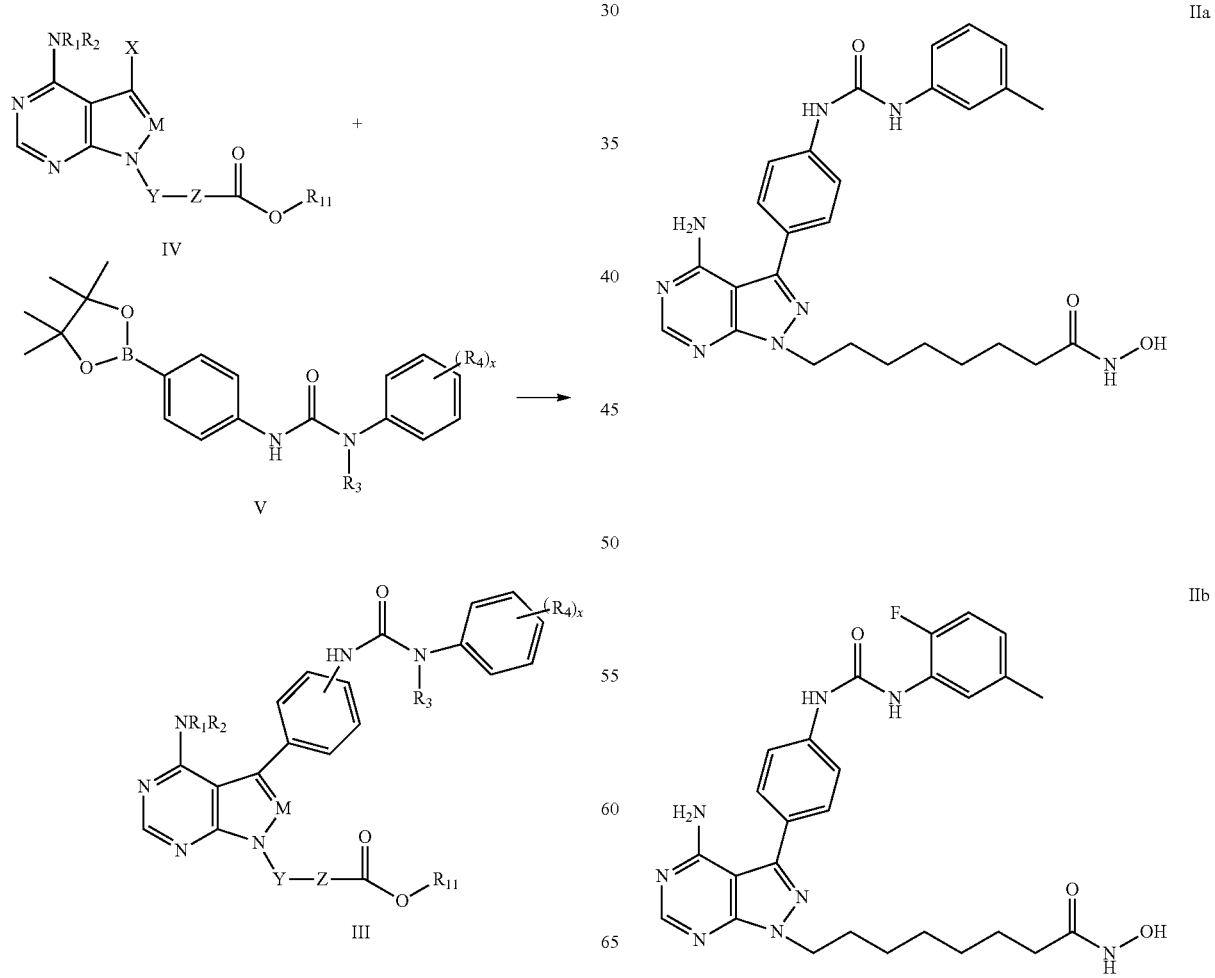

in formula IV, $R_1$, $R_2$, M, Y, Z and $R_{11}$ are defined as in formula III, X is chloro, bromo or iodo;

in formula V, $R_3$, $R_4$ and x are defined as in formula III.

Due to the use of the above technical schemes, the present invention has the following advantages over the prior art:

The compound provided by the present invention have three important targets in a body, both exerts a synergistic effect sufficiently to increase biological activity, and avoids problems caused by different properties and metabolisms, which is more practical and has good prospects.

DETAILED DESCRIPTION OF EMBODIMENTS

In the following, the present invention is explained in detail combining with the specific embodiments (Compound IIa, IIb, IIc and IId). It should be understood that these embodiments are used to illustrate the basic principles, the main features and advantages of the present invention, and should not be concluded as limitation. Implementation conditions used in embodiments may be adjusted according to specific requirements, and unspecified conditions usually are conditions used in conventional experiments.

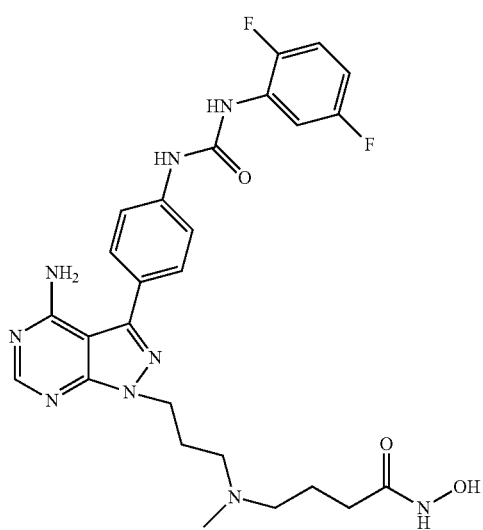
IIc
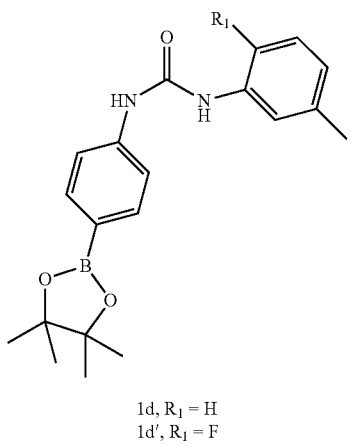
1d, R$_1$ = H
1d', R$_1$ = F
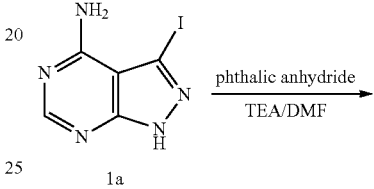
1a
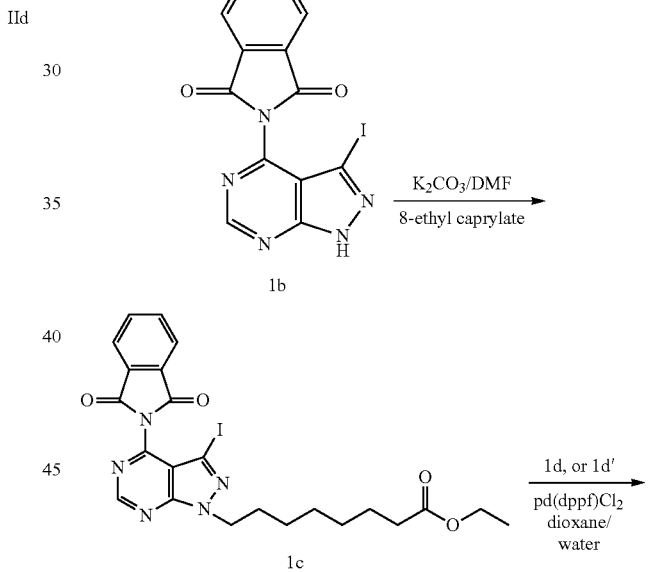
IId
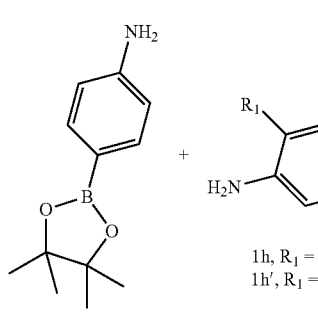
Compound IIa and compound IIb are synthesized according to the following synthetic routes:
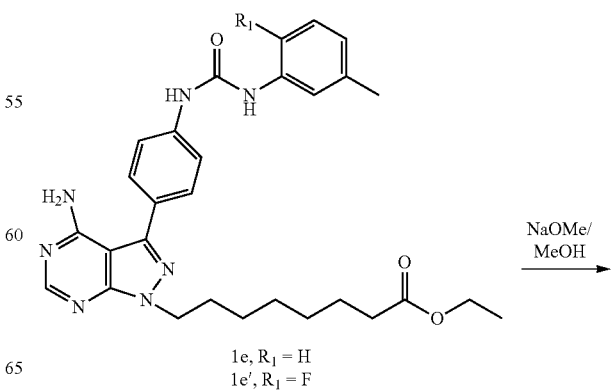
1e, R$_1$ = H
1e', R$_1$ = F

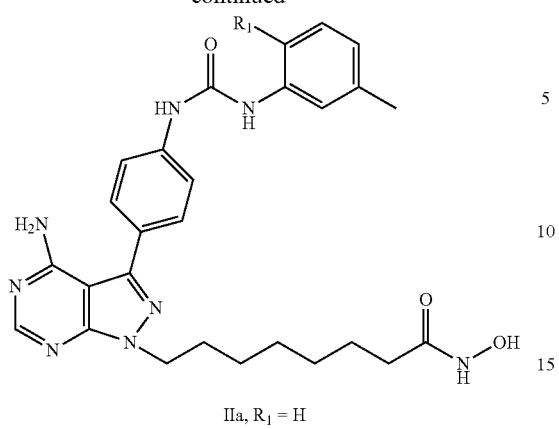
IIa, R₁ = H
IIb, R₁ = F
Compound IIc and compound IId are synthesized according to the following synthetic routes:
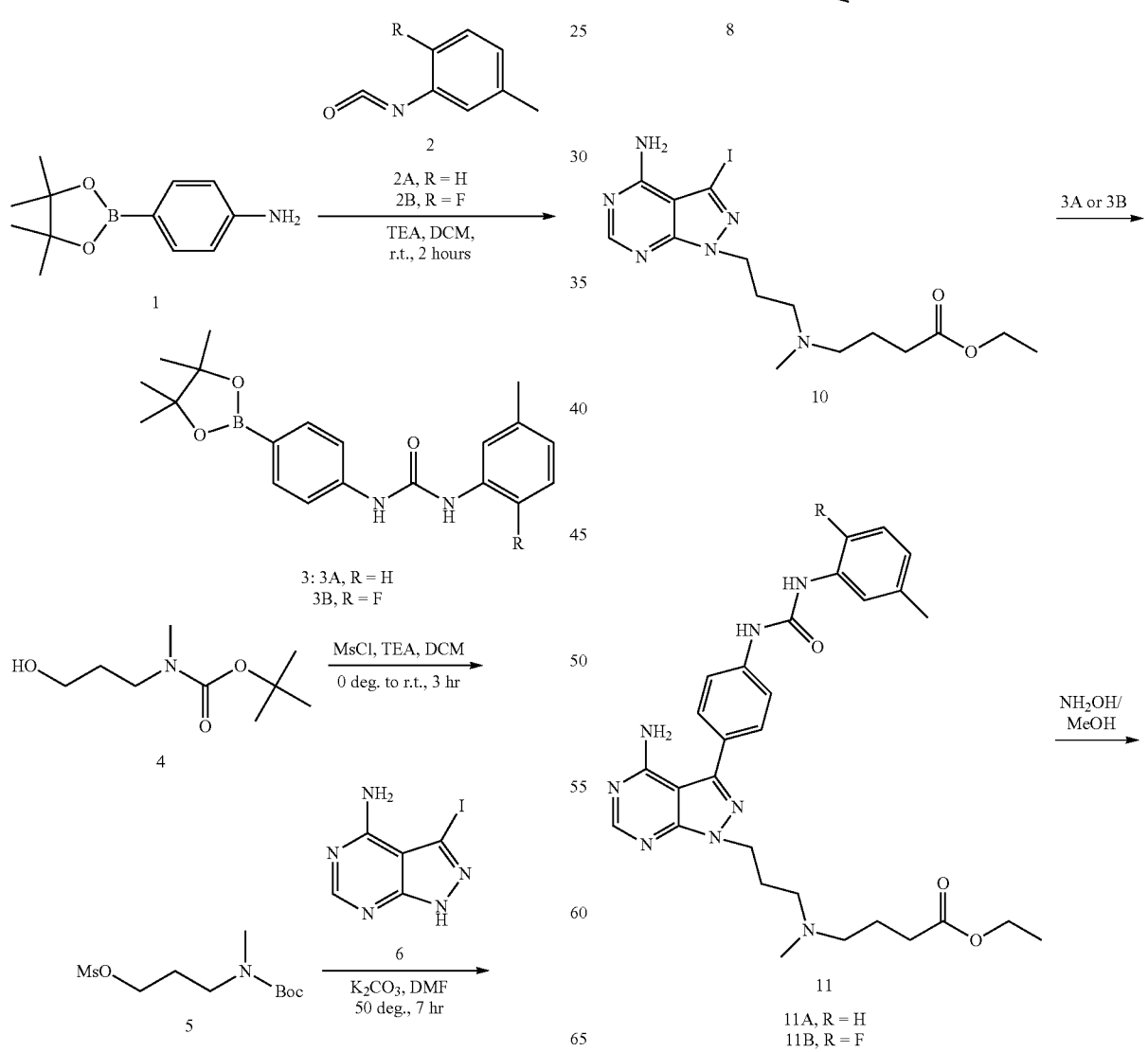
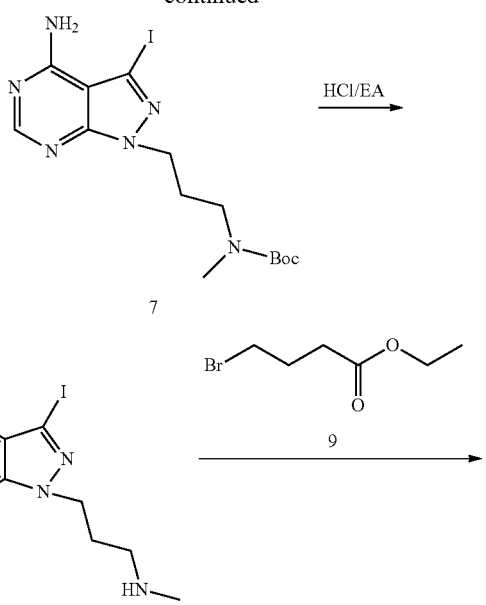

-continued

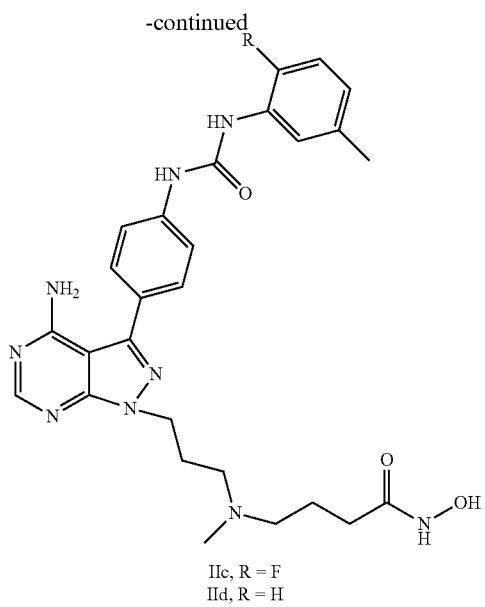

IIc, R = F
IId, R = H

Embodiment 1: Preparation of Compound 1b

Compound 1a (10 g, 0.038 mol), phthalic anhydride (11.2 g, 0.076 moL) and triethylamine (7.67 g, 0.076 moL) were dissolved in anhydrous DMF (180 mL), and the solution was heated to 100° C. for 10 hours, decompressed to remove the solvent, concentrated to give the crude product, mixed and purified by column chromatography (eluent was ethyl acetate:petroleum ether=1:1-1:0), and gray solid 1b was obtained (11.7 g, 78% yield);
$^1$H-NMR (d$_6$ DMSO, 400 MHz): δ=15.0 (s, 1H), 9.17 (s, 1H), 8.15-8.17 (m, 2H), 8.03-8.05 (m, 2H). LC-MS: 392 [M+1].

Embodiment 2: Preparation of Compound 1c

Compound 1b (391 mg, 1 mmoL) and K$_2$CO$_3$ (204 mg, 1.5 mmoL) were dissolved in anhydrous DMF (10 mL), and 8-ethyl caprylate (276 mg, 1.1 mmoL) was slowly dropwise added into the solution with nitrogen protection, and stirred for 16 hours at room temperature. The resulted system was regulated to pH=7-8 with 1M hydrochloric acid solution and extracted with ethyl acetate, then organic phases were merged and washed successively with water and saturated salt water, dried by anhydride Na$_2$SO$_4$, concentrated to give the crude product, mixed and purified by column chromatography (eluent was ethyl acetate:petroleum ether=10:1-5:1), and light yellow solid 1c was obtained (365 mg, 65% yield) LC-MS: 562 [M+1].

Embodiment 3: Preparation of Compound 1d

1-[4-(4,4,5,5-Tetramethyl-[1,3,2]dioxaborolan-2-yl)-phenyl]-3-m-tolyl-urea

Compound 1h (8.1 g, 0.0615 mol) and triethylamine (26 mL, 0.185 mol) were dissolved in anhydrous dichloromethane (300 mL), and cooled to 0° C. Compound 1f (9 g, 0.041 mmol) was slowly dropwise added into the solution. The resulted system was naturally raised to room temperature, stirred for 2 hours, quenched by adding saturated sodium bicarbonate solution, and then extracted with dichloromethane. Then organic phases were merged and washed successively with water and saturated salt water for 3 times, concentrated to give the crude product, mixed and purified by column chromatography (eluent was petroleum ether:ethyl acetate=2:1), and white solid 1d was obtained (9.2 g, 65% yield) LC-MS: 353 [M+1].

Embodiment 4: Preparation of Compound 1e

Compound 1c (8.2 g, 0.0146 mol), compound 1d (7.7 g, 0.0219 mol) and Na$_2$CO$_3$ (3.09 g, 0.0292 mol) were dissolved in a system of water/1, 4-dioxane (10 mL/100 mL), and then nitrogen displacement was performed for 3 times. Pd (dppf)Cl$_2$.CH$_2$Cl$_2$ (1.19 g, 0.00146 mol) was added into the solution under nitrogen protection. The resulted system was risen to 80° C. for 16 hours, added with ethyl acetate, washed successively with water and saturated salt water for 3 times, dried by anhydride Na$_2$SO$_4$, concentrated to give the crude product, mixed and purified by column chromatography (eluent was methyl alcohol:dichloromethane=20:1), and gray black solid 1e was obtained (4.7 g, 61% yield), LC-MS: 530 [M+1].

Embodiment 5: Preparation of Compound IIa

NH$_2$OH HCl (2.6 g, 0.373 mol) was heated and dissolved into anhydride MeOH (20 mL), and new-made NaOMe (0.8 mol) was added in at 50° C., then kept the temperature at 55° C. for 30 min, cooled to room temperature, and filtered to remove solid substance. Compound 1e (4.2 g, 0.08 mol) was added into filtered liquor, and the solution was risen to 50° C. for 16 hours, regulated to pH=5-6 with 1M hydrochloric acid solution, concentrated to give the crude product, mixed and purified by column chromatography (eluent was methyl alcohol:dichloromethane=20:1), and gray white solid, i.e. compound IIa was obtained (3.0 g, 73% yield); $^1$H-NMR (d$_6$ DMSO, 400 MHz): δ=10.3 (s, 1H), 8.95 (s, 1H), 8.68-8.72 (m, 2H), 8.25 (s, 1H), 7.50-7.68 (m, 4H), 7.32 (s, 1H), 7.15-7.27 (m, 2H), 6.80 (d, J=2.8 Hz, 1H), 4.32 (t, 2H), 2.29 (s, 3H), 1.83-1.93 (m, 4H) 1.45-1.47 (m, 2H), 1.24-1.28 (m, 6H). LC-MS: 517 [M+1].

Embodiment 6: Preparation of Compound 1d'

Compound 1h' (7.68 g, 0.0615 mol) and triethylamine (26 mL, 0.185 mol) were dissolved in anhydrous dichloromethane (300 mL), and cooled to 0° C. Compound 1f (9 g, 0.041 mmol) was slowly dropwise added into the solution. The resulted system was naturally raised to room temperature, stirred for 2 hours, quenched by adding saturated sodium bicarbonate solution, and then extracted with dichloromethane. Then organic phases were merged and washed successively with water and saturated salt water for 3 times, concentrated to give the crude product, mixed and purified by column chromatography (eluent was petroleum ether:ethyl acetate=2:1), and white solid 1d' was obtained (7.2 g, 48% yield). $^1$HNMR (CDCl$_3$, 400 MHz): δ=7.88 (d, J=3.6 Hz, 1H), 7.76-7.78 (m, 2H), 7.37-7.39 (m, 2H), 7.05-7.07 (m, 2H), 6.90-6.93 (m, 1H), 6.80-6.81 (m, 1H), 2.29 (s, 3H), 1.35 (s, 12H). LC-MS: 371 [M+1]+.

Embodiment 7: Preparation of Compound 1e'

Compound 1c (8.2 g, 0.0146 mol), compound 1d' (6.48 g, 0.0175 mol) and Na$_2$CO$_3$ (3.09 g, 0.0292 mol) were dissolved in a solution of water/1, 4-dioxane (10 mL/100 mL), and then nitrogen displacement was performed for 3 times.

Pd (dppf) Cl$_2$.CH$_2$Cl$_2$ (1.19 g, 0.00146 mol) was added into the obtained system sunder nitrogen protection. The resulted system was risen to 85° C. and stirred for 16 hours, added with ethyl acetate, washed successively with water and saturated salt water for 3 times, dried by anhydride Na$_2$SO$_4$, concentrated to give the crude product, mixed and purified by column chromatography (eluent was methyl alcohol:dichloromethane=20:1), and gray solid 1e' was obtained (5.1 g, 64% yield), LC-MS: 548 [M+1]$^+$.

Embodiment 8: Preparation of Compound IIb

NH$_2$OH HCl (1.97 g, 0.028 mol) was heated and dissolved in anhydride MeOH (15 mL), and new-made NaOMe (0.6 mol) was added in at 50° C., then kept the temperature at 55° C. for 30 min, cooled to room temperature, and filtered to remove solid. Compound 1e' (3.3 g, 0.06 mol) was added into filtered liquor, and the solution was risen to 50° C. for 16 hours, regulated to pH=5-6 with 1M hydrochloric acid solution, concentrated to give the crude product, mixed and purified by column chromatography (eluent was methyl alcohol:dichloromethane=20:1), and gray white solid, i.e. compound IIb was obtained (0.72 g, 22% yield).

$^1$H-NMR (DMSO-d$_6$, 400 MHz): δ=10.3 (s, 1H), 9.28 (s, 1H), 8.64 (d, J=1.2 Hz, 1H), 8.55 (d, J=1.2 Hz, 1H), 8.24 (s, 1H), 8.00-8.02 (m, 1H), 7.58-7.64 (m, 4H), 7.09-7.14 (m, 1H), 6.81 (m, 1H), 4.31 (t, 2H), 2.28 (s, 3H), 1.82-1.93 (m, 4H), 1.43-1.47 (m, 2H), 1.97-1.27 (m, 6H); LC-MS: 535 [M+]$^+$.

Embodiment 9: Preparation of Compound 3A

Compound 1 (15 g, 68.5 mmol) and triethylamine (28.75 mL, 205.5 mmol) were dissolved in 300 mL anhydrous dichloromethane. Under nitrogen protection, compound 2A (11.4 g, 76.35 mmol) was dissolved in 30 mL dichloromethane and added into the above reaction system, stirred at room temperature overnight. After the reaction, the solution was concentrated to give the crude product, mixed, separated and purified by silica-gel column chromatography (ethyl acetate/petroleum ether=1/10-1/3), and light white solid 3, i.e. compound 3A was obtained, 93.9% yield. LC-MS: 353.1 [M+1].

Embodiment 10: Preparation of Compound 3B

Compound 1 (15 g, 68.5 mmol) and triethylamine (28.75 mL, 205.5 mmol) were dissolved in 300 mL anhydrous dichloromethane. Under nitrogen protection, compound 2B (11.4 g, 76.35 mmol) dissolved in 30 mL dichloromethane was dropwise added into the above reaction system, and stirred at room temperature overnight. After the reaction, the system was concentrated to give the crude product, mixed, separated and purified by silica-gel column chromatography (ethyl acetate/petroleum ether=1/10-1/3), and off-white solid 3, i.e. compound 3B was obtained, 93.9% yield. LC-MS: 371.1 [M+1].

Embodiment 11: Preparation of Compound 5

Compound 4 (10 g, 53 mmol) and triethylamine (22.1 mL, 159 mmol) were dissolved in 300 mL anhydrous dichloromethane. Under nitrogen protection, methylsulfonyl chloride (7.85 g, 68.9 mmol) was dissolved in 30 mL dichloromethane and added into the above solution, and stirred at 0° C. for 1 hour. After the reaction, the system was extracted, and then the organic phase was washed with water and saturated salt water, dried and filtered, and light white solid compound 5 was obtained (13 g, 97.8% yield). LC-MS: 196 [M+1-56].

Embodiment 12: Preparation of Compound 7

Compound 5 (5 g, 19 mmol) was dissolved in 400 mL dried DMF, and then K$_2$CO$_3$ (3.15 g, 22.8 mmol) and compound 5 (5.95 g, 22.8 mmol) were added into the above reaction system. The system was stirred for 4 hours at 50° C., and detected the end of the reaction by LC-MS. The system was added with 200 mL water, and then extracted with ethyl acetate (300 mL×2). Then organic phases were merged and washed successively with water and saturated salt water, dried by anhydrous Na$_2$SO$_4$, and concentrated to give the crude product compound 7 without purification and directly used in the next step.

Embodiment 13: Preparation of Compound 8

Compound 7 dissolved in 100 mL hydrochloric acid/ethyl acetate, stirred for 1 hour under nitrogen protection, and filtered to give hydrochloride of compound 8 which was directly used in the next step.

Embodiment 14: Preparation of Compound 10

2.4 g hydrochloride of compound 8 dissolved in 40 mL dried DMF, then K$_2$CO$_3$ (9.17 g, 66.5 mmol) was added in, and 4-bromo-butyric acid ethyl ester, i.e. compound 9 (4.43 g, 22.8 mmol) was dropwise added into the above reaction system and then stirred at room temperature overnight. LC-MS was used to detect the end of reaction. The system was added with 200 mL water, and then extracted with ethyl acetate (300 mL×2). Then organic phases were merged and washed with water and saturated salt water, dried by anhydrous Na$_2$SO$_4$, concentrated to give the crude product, mixed and purified by silica-gel column chromatography (ethyl acetate/petroleum ether=1/1), and compound 10 was obtained (2.1 g, 72.4% yield). LCMS: 447 [M+1]$^+$.

Embodiment 15: Preparation of Compound 11B

Compound 10 (1.25 g, 2.8 mmol) and compound 3B (1.251 g, 3.36 mmol) were dissolved in ethyl alcohol/water (20 mL/10 mL), and then TEA (1.17 mL, 8.4 mmol) and Pd(dppf) Cl$_2$.CH$_2$Cl$_2$ (450 mg, 0.59 mmol) were added in, and the solution was refluxed for 2 hours under nitrogen protection. The resulted system was extracted with ethyl acetate for 2 times, and then the organic phases were washed with water and saturated salt water, dried, concentrated to give the crude product, mixed and purified by silica-gel column chromatography (ethyl acetate/petroleum ether=2/1), and compound 11B was obtained (900 mg, 57.3% yield), LCMS: 563 [M+1]$^+$.

Embodiment 15: Preparation of Compound IIc 900 mg compound 11B (1.6 mmol) was dissolved in 20 mL 1.6M hydroxylamine methanol solution and then stirred at room temperature for 2 hours. After the reaction, the system was concentrated, rotarily dried and purified by high pressurized liquor chromatography to give compound IIc (230 mg, 26.1% yield).

$^1$H-NMR (DMSO-d6, 400 MHz): δ=9.27 (s, 1H), 8.54-8.64 (d, 2H), 8.24 (s, 1H), 7.99-8.02 (d, 2H), 7.58-7.64 (m, 4H), 7.09-7.14 (m, 1H), 6.80-6.83 (m, 1H), 4.33-4.37 (t,

2H), 2.22-2.33 (m, 7H), 2.11 (t, 3H), 1.92-1.98 (m, 4H), 1.58-1.63 (m, 2H); LC-MS: 550 [M+1]$^+$.

Embodiment 16: Preparation of Compound 11A

Compound 10 (800 mg, 1.79 mmol) and compound 3A (0.8 g, 2.14 mmol) were dissolved in ethyl alcohol/H$_2$O (20 mL/10 mL), and then TEA (1.17 mL, 8.4 mmol) and Pd(dppf)Cl$_2$.CH$_2$Cl$_2$ (450 mg, 0.59 mmol) were added in, and the solution was refluxed for 2 hours under nitrogen protection. The resulted system was extracted with ethyl acetate for 2 times, and then the organic phases were washed with water and saturated salt water, dried, concentrated to give the crude product, mixed and purified by silica-gel column chromatography (ethyl acetate/petroleum ether=2/1), and compound 11A was obtained (900 mg, 57.3% yield), LC-MS: 545 [M+1]$^+$.

Embodiment 17: Preparation of Compound IId 650 mg compound 11A (1.19 mmol) was dissolved in 1.61M hydroxylamine methanol solution and then stirred at room temperature for 2 hours. After the reaction, the system was concentrated, rotarily dried and purified by high pressurized liquor chromatography to give compound IIc (100 mg, 15.8% yield).

$^1$H-NMR (DMSO-d6, 400 MHz): δ=10.34 (s, 1H), 9.05 (s, 1H), 8.28 (s, 1H), 8.24 (s, 1H), 7.56-7.65 (m, 4H), 7.32 (s, 1H), 7.25-7.27 (d, 1H), 7.14-7.18 (t, 1H), 6.79-6.80 (d, 1H), 4.33-4.37 (t, 2H), 2.22-2.33 (m, 7H), 2.11 (t, 3H), 1.92-1.98 (m, 4H), 1.58-1.63 (m, 2H); LC-MS: 532 [M+1]$^+$.

Embodiment 18: Inhibition of Compound IIa, IIb, IIc and IId on the Activity of Catalyzing Substrate Phosphorylation of KDR (VEGFR2) Protein Tyrosine Kinase at the Molecular Level: Enzyme-Linked Immunosorbent Assay (ELISA)

1. Main Instruments
Tunable wavelength type microplate reader (Molecular Devices SPECTRAMAX190)
2. Main Reagents
The tyrosine kinase VEGFR2 was expressed by utilizing the insect baculovirus expression system and affinity purified by Ni-NTA column in our laboratory, and met the experimental requirements by detection;
Kinase reaction substrate Poly(Glu, Tyr)$_{4:1}$ (SIGMA);
Anti-phosphorylation tyrosine monoclonal antibody PY99 (SANTA CRUZ);
Horseradish peroxidase labeled Sheep anti mouse IgG (CALBIOCHEM);
ATP, DTT, OPD (AMRESCO);
Enzyme labeled plate (CORNING);
Su11248 (Sunitinib) (LC LABORATORIES)
Compound IIa (prepared according to the present invention);
Compound IIb (prepared according to the present invention);
Compound IIc (prepared according to the present invention);
Compound IId (prepared according to the present invention);
Other reagents made in china.
3. Experimental Procedures
(1) Kinase reaction substrate Poly(Glu,Tyr)$_{4:1}$ was diluted to 20 g/ml with potassium ion-free PBS, and enzyme labeled plate was coated by the substrate, reacted at 37° C. for 12-16 h, and then the liquid in holes was removed.
(2) Enzyme labeled plate was washed with T-PBS for 10 min three times.
(3) Enzyme labeled plate was dried at 37° C. in a dryer.
(4) The tested samples were added into holes of the coated enzyme labeled plate:
The tested samples was firstly formulated to be a 10$^{-2}$ M stock solution in DMSO, subpackaged and storaged at −20° C., and then diluted to required concentration with reaction buffer before use, added into the experiment holes to reach corresponding final concentration in a 100 μL reaction system. Meanwhile, positive control holes were created, and added with positive control compound Su11248.
(5) Adding ATP and the tested tyrosine kinase:
ATP solution (final concentration 5 μM) diluted with reaction buffer was added, and then tested tyrosine kinase diluted with reaction buffer was added. Total volume of the reaction system was 100 μL. Meanwhile, negative control holes and enzyme-free control holes were created.
(6) The reaction systems were placed in a wet box, reacted at 37° C. on a shaking table for 1 hour under a condition that light was prohibited, and after the reaction, the plate was washed with T-PBS for three times.
(7) Antibody PY99 100 μL/hole was added, reacted at 37° C. on a shaking table for 30 minutes. The plate was washed for three times with T-PBS.
(8) Horseradish peroxidase labeled Sheep anti mouse IgG 100 μL/hole was added, and reacted at 37° C. on a shaking table for 30 minutes. The plate was washed for three times with T-PBS.
(9) OPD coloring solution 100 μL/hole was added, and reacted at room temperature for 1-10 minutes under a condition that light was prohibited.
(10) 2M H$_2$SO$_4$ 50 μL was added to terminate the reaction, and value A$_{490}$ was measured by tunable wavelength type micro plate (Molecular Devices SPECTRAMAX190).
(11) The inhibition rate of the sample was obtained by the following equation:

$$\text{Inhibition Rate of Sample \%} = \left(1 - \frac{OD \text{ value of compound} - OD \text{ value of enzyme-free control hole}}{OD \text{ value of negative control hole} - OD \text{ value of enzyme-free control hole}}\right) \times 100\%$$

Experimental Result

| Inhibition rate to the activity of VEGFR2 tyrosine kinase(%) | |
| --- | --- |
| Compound | IC$_{50}$ (nM) |
| IIa | 3.0 ± 1.0* |
| IIb | 2.2 ± 0.9* |
| IIc | 572** |
| IId | 1194** |
| Sunitinib (Su11248, control drug) | 6.4 ± 3.3* |

*IC$_{50}$ is the average of the three experimental results ± SD.
**IC$_{50}$ is a result from one experiment.

Experiment Conclusions

In this experiment, the positive control compounds (clinical drug) Sunitinib obtained a result of 6.4±3.3 nM, in compliance with the reference range and reliable.

The experiments confirmed that the tested samples IIa and IIb can significantly inhibit the activity of VEGFR2 tyrosine kinase at the molecular level. The tested samples IIc and IId can also well inhibit the activity of VEGFR2 tyrosine kinase.

Embodiment 19: Inhibition of Compound IIa, IIb, IIc and IId on the Activity of Catalyzing Substrate Phosphorylation of PDGFR-β (Platelet-Derived Growth Factor Receptor β) Protein Tyrosine Kinase at the Molecular Level: Enzyme-Linked Immunosorbent Assay (ELISA)

1. Main Instruments
Tunable wavelength type microplate reader (Molecular Devices SPECTRAMAX190)
2. Main Reagents
Tyrosine kinase PDGFR-β (MILLIPORE);
Kinase reaction substrate Poly(Glu,Tyr)$_{4:1}$ (SIGMA);
Anti-phosphorylation tyrosine monoclonal antibody PY99 (SANTA CRUZ);
Horseradish peroxidase labeled Sheep anti mouse IgG (CALBIOCHEM);
ATP, DTT, OPD (AMRESCO);
Enzyme labeled plate (CORNING);
Su11248 (LC LABORATORIES)
Other reagents made in china.
3. Experimental Procedures
(1) Kinase reaction substrate Poly(Glu,Tyr)$_{4:1}$ was diluted to 20 g/ml with potassium ion-free PBS, and enzyme labeled plate was coated by the substrate, reacted at 37° C. for 12-16 h, and then the liquid in holes was removed.
(2) Enzyme labeled plate was washed with T-PBS for 10 min three times.
(3) Enzyme labeled plate was dried at 37° C. in a dryer.
(4) The tested samples were added into holes of the coated enzyme labeled plate:
The tested samples were firstly formulated to be a $10^{-2}$ M stock solution in DMSO, subpackaged and stored at −20° C., and then diluted to required concentration with reaction buffer before use, added into the experiment holes to reach corresponding final concentration in a 100 μL reaction system. Meanwhile, positive control holes were created, and positive control compound Su11248 was added.
(5) Adding ATP and the tested tyrosine kinase:
ATP solution (final concentration 5 μM) diluted with reaction buffer was added, and then tested tyrosine kinase diluted with reaction buffer was added. Total volume of the reaction system was 100 μL. Meanwhile, negative control holes and enzyme-free control holes were created.
(6) The reaction system were placed in a wet box, reacted at 37° C. on a shaking table for 1 hour under a condition that light was prohibited, and after the reaction, the plate was with T-PBS washed for three times.
(7) Antibody PY99 100 μL/hole was added, and reacted at 37° C. on a shaking table for 30 minutes. The plate was washed for three times with T-PBS.
(8) Horseradish peroxidase labeled Sheep anti mouse IgG 100 μL/hole was added, and reacted at 37° C. on a shaking table for 30 minutes. The plate was washed for three times with T-PBS.
(9) OPD coloring solution 100 μL/hole was added, and reacted at room temperature for 1-10 minutes under a condition that light was prohibited.
(10) 2M $H_2SO_4$ 50 μL was added to terminate the reaction, and value $A_{490}$ was measured by tunable wavelength type micro plate (Molecular Devices SPECTRAMAX190).

(11) The inhibition rate of the sample was obtained by the following equation:

$$\text{Inhibition Rate of Sample \%} = \left(1 - \frac{OD \text{ value of compound} - OD \text{ value of enzyme-free control hole}}{OD \text{ value of negative control hole} - OD \text{ value of enzyme-free control hole}}\right) \times 100\%$$

Experimental Result

| Inhibition rate to the activity of PDGFR-β tyrosine kinase | |
|---|---|
| Compound | IC$_{50}$ (nM) |
| IIa | 2.9 ± 1.5* |
| IIb | 0.5 ± 0.1* |
| IIc | 146** |
| IId | 99.9** |
| Sunitinib (Su11248, control drug) | 2.3 ± 1.1* |

*IC$_{50}$ is the average of the three experimental results ± SD.
**IC$_{50}$ is a result from one experiment.

Experiment Conclusions
In this experiment, the positive control compounds (clinical drug) Sunitinib obtained a result of 2.3+1.1 nM, in compliance with the reference range and reliable. The experiments confirmed that the tested samples IIa and IIb can significantly inhibit the activity of PDGFR-β tyrosine kinase at the molecular level. The tested samples IIc and IId can also well inhibit the activity of PDGFR-β tyrosine kinase.

Embodiment 20: Inhibition of Compounds of Different Concentrations on the Catalyzing Activity of Histone Deacetylase 1 (HDAC1): Fluorescence Detection 1. Main Instruments
Fluorescence microplate reader Envision (PREKINELMER, USA)
2. Main Reagents
Human HDAC1, obtained by utilizing baculovirus expression system;
Substrate, Ac-Lys-Tyr-Lys (Ac)-AMC;
SAHA (Vorinostat) (LC LabORATORIES);
Compound IIa (prepared according to the present invention);
Compound IIb (prepared according to the present invention);
Compound IIc (prepared according to the present invention);
Compound IId (prepared according to the present invention);
3. Main Procedures
Enzymatic activity was tested in 96-well or 384-well flat microwell plate by fluorescence detection and taking Ac-Lys-Tyr-Lys(Ac)-AMC as substrate. The tested samples was firstly formulated to be a $10^{-2}$ M stock solution in DMSO, subpackaged and stored at −20° C., and then diluted to required concentration with reaction buffer before use. Substrate Ac-Lys-Tyr-Lys (Ac)-AMC was deacetylated by HDAC1, and the fluorescence signal of the product AMC obtained by enzyme hydrolysis was detected at 355 nm or 460 nm by a fluorescence detector. The initial reaction speed was calculated by detecting the change of fluorescence signal with time.

Experimental Result

Experimental result was as follow:

Inhibition rate to the activity of histone deacetylase 1(HDAC1) (%)

| Compound | three experimental results $IC_{50}$ (μM) |
|---|---|
| IIa | 1.09 ± 0.21* |
| IIb | 0.47 ± 0.07* |
| IIc | 8.65** |
| IId | 13.8** |
| SAHA (Vorinostat, control drug) | 0.23 ± 0.04* |

*$IC_{50}$ is the average of the three experimental results ±SD.
**$IC_{50}$ is a result from one experiment.

Experiment Conclusions

In this experiment, $IC_{50}$ of the positive control compounds SAHA was 0.23+0.04 μM, in compliance with the reference range and reliable. Therefore, the experiments confirmed that the tested samples IIa and IIb can significantly inhibit the activity of HDAC1 at the molecular level. The tested samples IIc and IId can also well inhibit the activity of HDAC1.

In the present invention, the $IC_{50}$±SD value and inhibition rate were the average values of 3-4 experiments carried out in different time. Wherein, each tested samples were tested at least two times.

The above experiments confirmed that the new hydroximic acid derivatives according to the present invention have inhibition to histone deacetylase 1 (HDAC1) and two kinds of tyrosine kinase (vascular endothelial cell growth factor receptors (VEGFR2) as well as platelet-derived growth factor receptors (PDPDGFR-β)) simultaneously, and confirmed that the new hydroximic acid derivatives (including their pharmaceutically acceptable salts and their pro-drugs, etc.) according to the present invention is a new kind of inhibitor with multiple targets and have pharmacological actions of both Sunitinib and Vorinostat. Therefore, they may be used for treating diseases mediated by tyrosine kinase and/or histone deacetylase, malignancies or eye diseases raised from pathologic neovascularization. Malignancies to be treated include, but not limited to, kidney cancer, liver cancer, colon cancer, gastrointestinal stromal tumor, non-small cell lung cancer, breast cancer, pancreatic cancer, neural glial tumor, lymph cancer, fibrosarcoma, ovarian cancer, leukemia and prostate cancer, etc. Eye diseases to be treated include age-related macular degeneration, diabetic retinopathy and neovascular glaucoma and the like.

The embodiments described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

What is claimed is:

1. A compound of formula I, and a pharmaceutically acceptable salt and a hydrate thereof,

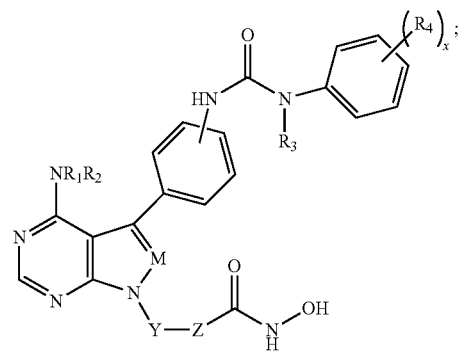

wherein in formula I,
  $R_1$, $R_2$ and $R_3$ are independently selected from hydrogen, alkyl and hetero alkyl;
  $R_4$ is selected from the group consisting of: halogen; hydroxyl; sulfhydryl; cyano; amino or alkyl-substituted amino; nitryl; $C_1$-$C_6$ alkyl unsubstituted or substituted by one or more of halogen, hydroxyl, sulfhydryl, cyano, amino, alkyl-substituted amino and nitryl; $C_1$-$C_6$ alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; $OCOR_9$; NHC(=O)OCH$_3$; NHC(=O)O CH$_2$CH$_3$;
  M is N or CH;
  Y is CH$_2$, CH(CH$_3$) or C=O;
  Z has a straight-chain structure consisting of 3-12 atoms and connecting Y and carbonyl of compound of formula I;
  x is an integer between 0 and 5; and
  $R_5$, $R_6$, $R_7$, $R_8$ and $R_9$ are independently selected from $C_1$-$C_6$ alkyl unsubstituted or substituted by halogen.

2. The compound of formula I according to claim 1, and the pharmaceutically acceptable salt and the hydrate thereof, wherein,
  in formula I,
  $R_1$, $R_2$ and $R_3$ are independently selected from hydrogen or $C_1$-$C_3$ alkyl;
  $R_4$ is selected from the group consisting of: fluoro, chloro, bromo, iodo, hydroxyl, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, C(=O)CH$_3$, C(=O)CH$_2$CH$_3$, C(=O)NHCH$_3$, C(=O) NHCH$_2$CH$_3$, NHC(=O)OCH$_3$, NHC(=O)O CH$_2$CH$_3$, NHCH$_3$, N(CH$_3$)$_2$, and NH CH$_2$CH$_3$;
  x is 0, 1, 2, 3 or 4;
  M, Y and Z are defined as in claim 1.

3. The compound of formula I according to claim 1, and the pharmaceutically acceptable salt and the hydrate thereof, wherein, in formula I, x is 1 or 2.

4. The compound of formula I according to claim 1, and the pharmaceutically acceptable salt and the hydrate thereof, wherein, the straight-chain structure consists of 3-8 carbon atoms as well as 0-4 oxygen atom(s) and/or nitrogen atom(s).

5. The compound of formula I according to claim 4, and the pharmaceutically acceptable salt and the hydrate thereof, wherein, the straight-chain structure consists of 4-7 carbon atoms as well as 0-2 oxygen atom(s) and/or nitrogen atom(s).

6. The compound of formula I according to claim 5, and the pharmaceutically acceptable salt and the hydrate thereof, wherein, the straight-chain structure consists of 5 or 6 carbon atoms as well as 0 or 1 oxygen atom and/or nitrogen atom.

7. The compound of formula I according claim 1, and the pharmaceutically acceptable salt and the hydrate thereof, wherein the straight-chain structure consists of 4-8 atoms.

8. The compound of formula I according to claim 1, and the pharmaceutically acceptable salt and the hydrate thereof, wherein, the straight-chain structure is a saturated or unsaturated $C_3$-$C_8$ alkyl straight chain uninterrupted or interrupted by 1-2 oxygen atom(s) and/or nitrogen atom(s).

9. The compound of formula I according to claim 8, and the pharmaceutically acceptable salt and the hydrate thereof, wherein, the straight-chain structure is a saturated or unsaturated $C_5$-$C_7$ alkyl straight chain uninterrupted or interrupted by 1-2 oxygen atom(s) and/or nitrogen atom(s).

10. The compound of formula I according to claim 1, and the pharmaceutically acceptable salt and the hydrate thereof, wherein in formula I, Z further includes one or two branch chain(s) connecting with the central section of the straight-chain structure, the branch chain(s) being a $C_1$-$C_6$ alkyl unsubstituted or substituted by halogen.

11. The compound of formula I according to claim 10, and the pharmaceutically acceptable salt and the hydrate thereof, wherein, the branch chain(s) is(are) methyl, ethyl or propyl.

12. The compound of formula I according to claim 1, and the pharmaceutically acceptable salt and the hydrate thereof, wherein, in formula I, Z is $(CH_2)_5$, $(CH_2)_6$, $(CH_2)_7$, $CH_2 CH_2 TCH_2 CH_2 CH_2$, $CH_2 CH_2 TCH_2 CH_2$ or $CH_2 CH_2 CH_2 TCH_2 CH_2 CH_2$, wherein T is O or $NR_{10}$, wherein $R_{10}$ is hydrogen, methyl, ethyl or propyl.

13. The compound of formula I according to claim 1, and the pharmaceutically acceptable salt and the hydrate thereof, wherein, the compound has a structure as shown in formula II:

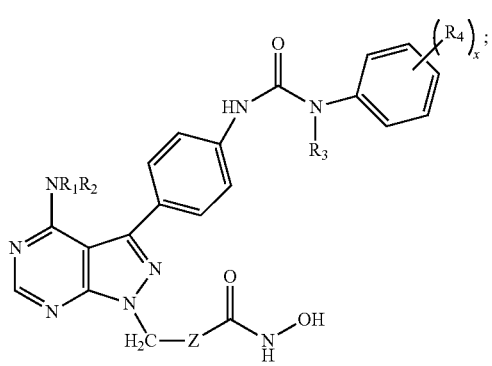

in formula II,
$R_1$, $R_2$ and $R_3$ are independently selected from hydrogen or $C_1$-$C_3$ alkyl;
$R_4$ is selected from the group consisting of: fluoro, chloro, bromo, iodo, hydroxy, sulfhydryl, cyano, amino, methylamino, ethylamino, nitryl, methyl, ethyl, isopropyl, trifluoromethyl, methoxy, trifluoromethoxy, ethoxy, hydroxymethyl, mercaptomethyl, $C(=O)CH_3$, $C(=O)CH_2CH_3$, $C(=O)$ $NHCH_3$, $C(=O)$ $NHCH_2CH_3$, $NHC(=O)OCH_3$, $NHC(=O)O$ $CH_2CH_3$, $NHCH_3$, $N(CH_3)_2$, and $NH$ $CH_2CH_3$;

Z has a straight structure connecting methylene and carbonyl, the straight-chain structure being a saturated or unsaturated $C_3$-$C_8$ alkyl straight chain uninterrupted or interrupted by 1-2 oxygen atom(s) and/or nitrogen atom(s); and x is 0, 1, 2, 3 or 4.

14. The compound of formula I according to claim 13, and the pharmaceutically acceptable salt and the hydrate thereof, wherein, the compound is a compound as shown in formula IIa, IIb, IIc and IId,

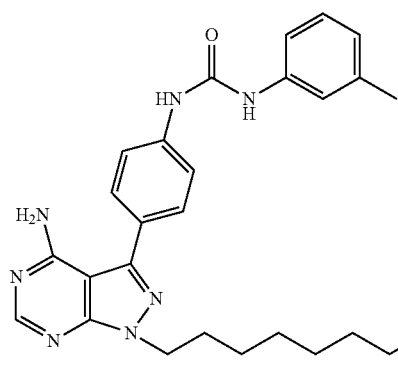

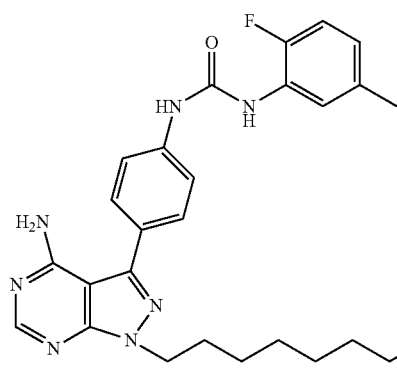

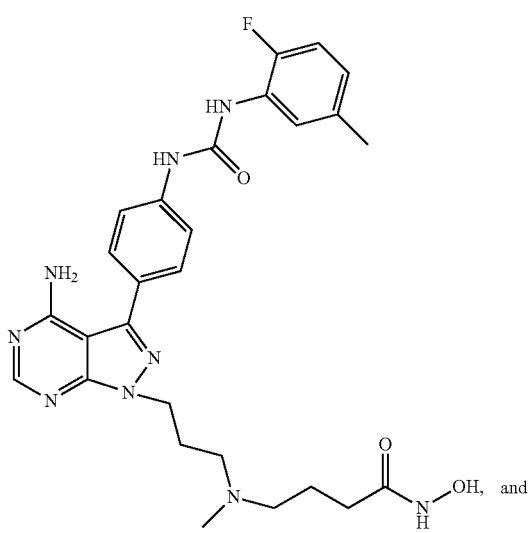

IId

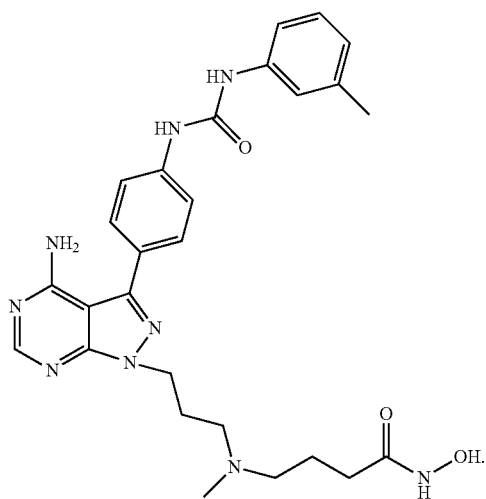

15. A method for inhibiting tyrosine kinase in a patient in need thereof by providing to said patient in an effective amount a compound of formula I, and a pharmaceutically acceptable salt and a hydrate thereof,

I

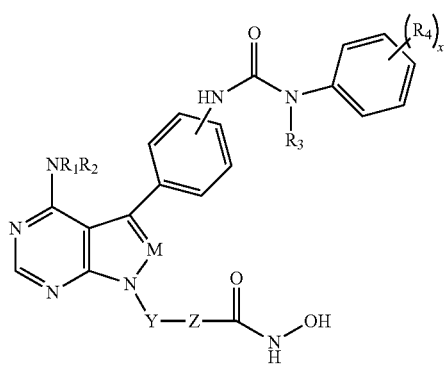

wherein in formula I,
R$_1$, R$_2$ and R$_3$ are independently selected from hydrogen, alkyl and hetero alkyl;
R$_4$ is selected from the group consisting of: halogen; hydroxyl; sulfhydryl; cyano; amino or alkyl-substituted amino; nitryl; C$_1$-C$_6$ alkyl unsubstituted or substituted by one or more of halogen, hydroxyl, sulfhydryl, cyano, amino, alkyl-substituted amino and nitryl; C$_1$-C$_6$ alkoxy unsubstituted or substituted by one or more of halogen, hydroxyl, sulfhydryl, cyano, amino, alkyl-substituted amino and nitryl; COR$_5$; CONHR$_6$; COOR$_7$; NHCOR$_8$; OCOR$_9$;
M is N or CH;
Y is CH$_2$, CH(CH$_3$) or C=O;
Z has a straight-chain structure consisting of 3-12 atoms and connecting Y and carbonyl of compound of formula I;
x is an integer between 0 and 5; and
R$_5$, R$_6$, R$_7$, R$_8$ and R$_9$ are independently selected from C$_1$-C$_6$ alkyl unsubstituted or substituted by halogen.

16. A pharmaceutical composition comprising the compound of formula I according to claim 1, and the pharmaceutically acceptable salt, and hydrate thereof.

17. A method of preparing a compound of formula I:

I

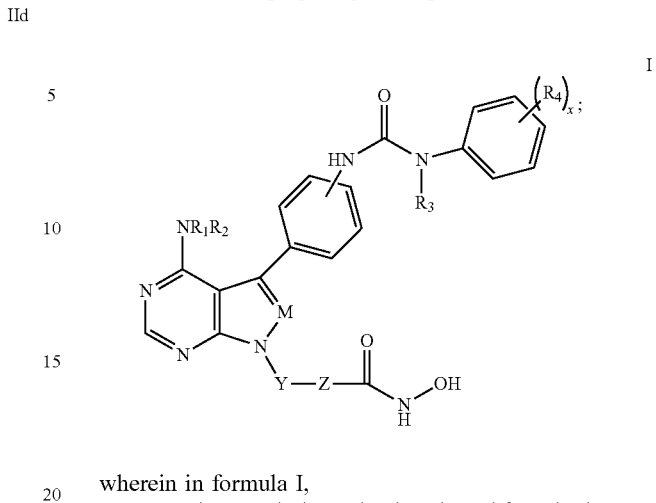

wherein in formula I,
R$_1$, R$_2$ and R$_3$ are independently selected from hydrogen, alkyl and hetero alkyl;
R$_4$ is selected from the group consisting of: halogen; hydroxyl; sulfhydryl; cyano; amino or alkyl-substituted amino; nitryl; C$_1$-C$_6$ alkyl unsubstituted or substituted by one or more of halogen, hydroxyl, sulfhydryl, cyano, amino, alkyl-substituted amino and nitryl; C$_1$-C$_6$ alkoxy unsubstituted or substituted by one or more of halogen, hydroxyl, sulfhydryl, cyano, amino, alkyl-substituted amino and nitryl; COR$_5$; CONHR$_6$; COOR$_7$; NHCOR$_8$; OCOR$_9$; NHC(=O)OCH$_3$; NHC(=O)OCH$_2$CH$_3$;
M is N or CH;
Y is CH$_2$, CH(CH$_3$) or C=O;
Z has a straight-chain structure consisting of 3-12 atoms and connecting Y and carbonyl of compound of formula I;
x is an integer between 0 and 5;
R$_5$, R$_6$, R$_7$, R$_8$ and R$_9$ are independently selected from C$_1$-C$_6$ alkyl unsubstituted or substituted by halogen;
by reacting the compound of formula III,

III

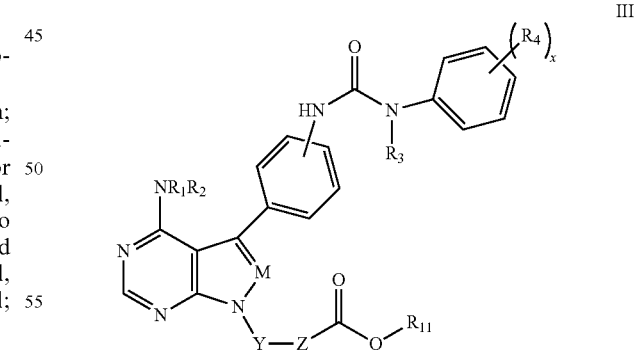

with a hydroxylamine methanol solution with stirring at room temperature,
in formula III,
R$_3$ are independently selected from hydrogen, alkyl and hetero alkyl;
R$_4$ is selected from the group consisting of: halogen; hydroxyl; sulfhydryl; cyano; amino or alkyl-substituted amino; nitryl; C$_1$-C$_6$ alkyl unsubstituted or substituted by one or more of halogen, hydroxyl, sulfhydryl, cyano, amino, alkyl-substituted amino and nitryl; $C_1$-$C_6$ alkoxy unsubstituted or substituted by one or more of halogen, hydroxyl, sulfhydryl, cyano, amino, alkyl-substituted amino and nitryl; $COR_5$; $CONHR_6$; $COOR_7$; $NHCOR_8$; $OCOR_9$; $NHC(=O)OCH_3$; $NHC(=O)O\ CH_2CH_3$;

M is N or CH;

Y is $CH_2$, $CH(CH_3)$ or C=O;

Z has a straight-chain structure consisting of 3-12 atoms and connecting Y and carbonyl of compound of formula I;

x is an integer between 0 and 5;

$R_5$, $R_6$, $R_7$, $R_8$ and $R_9$ are independently selected from $C_1$-$C_6$ alkyl unsubstituted or substituted by halogen;

$R_{11}$ is $C_1$-$C_6$ alkyl unsubstituted or substituted by halogen; and when neither of $R_1$ and $R_2$ is hydrogen, $R_1$ and $R_2$ are defined as in formula I; and when at least one of $R_1$ and $R_2$ is hydrogen, $R_1$ and $R_2$ are defined as in formula I, or at least one of $R_1$ and $R_2$ is amino protection group.

18. The method according to claim 17, the method comprising a step of producing the compound of formula III by dissolving a compound of formula IV with a compound of formula V in ethyl alcohol/water, adding TEA and Pd(dppf)$Cl_2.CH_2Cl_2$ in the solution, and refluxing the solution under nitrogen protection:

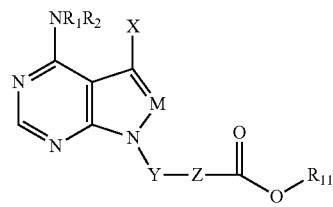

IV

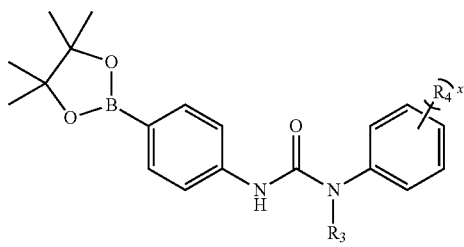

V

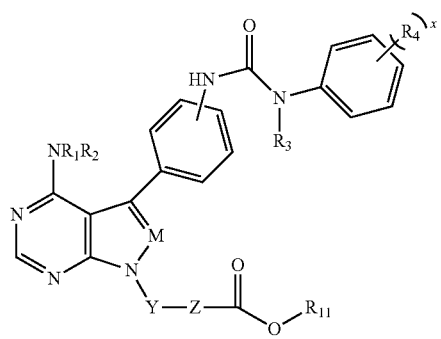

III in formula IV, $R_1$, $R_2$, M, Y, Z and $R_{11}$ are defined as in formula III, X is chloro, bromo or iodo; and in formula V, $R_3$, $R_4$ and x are defined as in formula III.

* * * * *